(12) United States Patent
Wang

(10) Patent No.: US 11,740,246 B2
(45) Date of Patent: *Aug. 29, 2023

(54) DUAL-COLUMN LC-MS SYSTEM AND METHODS OF USE THEREOF

(71) Applicant: Regeneron Pharmaceuticals, Inc., Tarrytown, NY (US)

(72) Inventor: Shunhai Wang, Ossining, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/872,679

(22) Filed: Jul. 25, 2022

(65) Prior Publication Data

US 2022/0357336 A1    Nov. 10, 2022

Related U.S. Application Data

(63) Continuation of application No. 17/125,342, filed on Dec. 17, 2020, now Pat. No. 11,435,359, which is a
(Continued)

(51) Int. Cl.
*G01N 33/68*      (2006.01)
*G01N 30/46*      (2006.01)
(Continued)

(52) U.S. Cl.
CPC ..... *G01N 33/6848* (2013.01); *B01D 15/1871* (2013.01); *C07K 1/16* (2013.01);
(Continued)

(58) Field of Classification Search
CPC ............. G01N 33/6848; G01N 30/462; G01N 30/465; G01N 30/468; G01N 30/482; G01N 30/7233; G01N 33/6821; G01N 30/463; G01N 2030/8831; B01D 15/1871; C07K 1/16; C07K 1/20
See application file for complete search history.

(56) References Cited

U.S. PATENT DOCUMENTS

| | | |
|---|---|---|
| 5,885,841 A | 3/1999 | Higgs, Jr. et al. |
| 8,017,015 B2 | 9/2011 | Clarke et al. |
| | (Continued) | |

FOREIGN PATENT DOCUMENTS

| | | |
|---|---|---|
| AR | 113730 A1 | 6/2020 |
| AU | 2019213643 A1 | 7/2020 |
| | (Continued) | |

OTHER PUBLICATIONS

Du Yiping, Modern Instrumental Analysis Methods, 1st Edition, China University of Science and Technology Press, pp. 86-87, Oct. 31, 2008.
(Continued)

*Primary Examiner* — Jennifer Wecker
*Assistant Examiner* — Michael Paul Shimek
(74) *Attorney, Agent, or Firm* — McCarter & English, LLP

(57) ABSTRACT

Methods for achieving complete sequence coverage of monoclonal antibodies by trypsin digestion and dual-column LC-MS system are provided. The disclosed method improves upon current techniques for standard peptide mapping.

20 Claims, 9 Drawing Sheets

Related U.S. Application Data continuation of application No. 16/260,471, filed on Jan. 29, 2019, now Pat. No. 10,908,166.

(60) Provisional application No. 62/624,352, filed on Jan. 31, 2018.

(51) Int. Cl.

| | | |
|---|---|---|
| *B01J 20/281* | (2006.01) | |
| *G01N 30/72* | (2006.01) | |
| *C07K 1/16* | (2006.01) | |
| *B01D 15/18* | (2006.01) | |
| *C07K 1/20* | (2006.01) | |
| *G01N 30/88* | (2006.01) | |

(52) U.S. Cl.
CPC .............. *C07K 1/20* (2013.01); *G01N 30/462* (2013.01); *G01N 30/465* (2013.01); *G01N 30/468* (2013.01); *G01N 30/482* (2013.01); *G01N 30/7233* (2013.01); *G01N 33/6821* (2013.01); *G01N 30/463* (2013.01); *G01N 2030/8831* (2013.01)

(56) References Cited

U.S. PATENT DOCUMENTS

| | | |
|---|---|---|
| 8,074,494 B2 | 12/2011 | Vorm et al. |
| 10,908,166 B2 | 2/2021 | Wang |
| 2002/0039747 A1 | 4/2002 | Lubman et al. |
| 2002/0150926 A1 | 10/2002 | Jindal et al. |
| 2005/0161399 A1 | 7/2005 | Dillon et al. |
| 2006/0118492 A1 | 6/2006 | Shieh et al. |
| 2006/0157647 A1 | 7/2006 | Siuzdak et al. |
| 2006/0169640 A1 | 8/2006 | Quinn |
| 2007/0233394 A1 | 10/2007 | Kangas et al. |
| 2008/0093300 A1 | 4/2008 | Clarke et al. |
| 2009/0145203 A1* | 6/2009 | Vorm .................. G01N 30/463 250/281 |
| 2010/0151584 A1 | 6/2010 | Parsons et al. |
| 2021/0009108 A1 | 1/2021 | Tsukano et al. |

FOREIGN PATENT DOCUMENTS

| | | |
|---|---|---|
| CA | 3084069 A1 | 8/2019 |
| CN | 101042377 A | 9/2007 |
| EP | 1426442 A1 | 6/2004 |
| JP | 2004-101477 A | 4/2004 |
| JP | 2017-508143 A | 3/2017 |
| TW | 201940883 A | 10/2019 |
| WO | 2004/017040 A2 | 2/2004 |
| WO | 2005/000226 A2 | 1/2005 |
| WO | 2006/084045 A1 | 8/2006 |
| WO | 2019/152352 A1 | 8/2019 |

OTHER PUBLICATIONS

Stavenhagen et al., Site-Specific Protein N- and O-Glycosylation Analysis by a C18-Porous Graphitized Carbon-Liquid Chromatography-Electrospray Ionization Mass Spectrometry Approach Using Pronase Treated Glycopeptides. Anal Chem. Dec. 1, 2015;87(23):11691-9.

Stavenhagen et al., Site-Specific N- and O-Glycopeptide Analysis Using an Integrated C18-PGC-LC-ESI-QTOF-MS/MS Approach. Methods Mol Biol. 2017;1503:109-119.

International Search Report and Written Opinion for Application No. PCT/US2019/015542, dated Apr. 11, 2019, 14 pages.

U.S. Notice of Allowance for U.S. Appl. No. 16/260,471, dated Oct. 5, 2020, 9 pages.

Lewandrowski et al., Online dual gradient reversed-phase/porous graphitized carbon nanoHPLC for proteomic applications. Anal Chem. Jun. 15, 2010;82(12):5391-6.

\* cited by examiner

| Mobile Phase | A: 0.05% TFA in Milli-Q water | | | | |
| --- | --- | --- | --- | --- | --- |
| | B: 0.045% TFA in Acetonitrile | | | | |
| Column | PGC: Hypercarb Porous Graphite Carbon Column 3 μm, 2.1mm x 30mm | | | | |
| | C18: ACQUITY UPLC BEH 130 C18 column, 1.7 μm, 2.1mm x 150mm | | | | |
| Gradient | Time (min) | Flow (mL/min) | %A | %B | |
| | 0 | 0.25 | 99.9 | 0.1 | ⎫ Typical C18 Peptide Mapping Run |
| | 5 | 0.25 | 99.9 | 0.1 | |
| | 80 | 0.25 | 65.0 | 35.0 | |
| | 85 | 0.25 | 10.0 | 90.0 | |
| | 90 | 0.25 | 10.0 | 90.0 | ⎭ |
| | 95 | 0.25 | 99.9 | 0.1 | ⎫ PGC Column Equilibration |
| | 100 | 0.25 | 99.9 | 0.1 | ⎭ |
| | 105 | 0.25 | 99.9 | 0.1 | ⎫ PGC Gradient |
| | 120 | 0.25 | 0.0 | 100.0 | |
| | 122 | 0.25 | 0.0 | 100.0 | |
| | 125 | 0.25 | 99.9 | 0.1 | |
| | 140 | 0.25 | 99.9 | 0.1 | ⎭ |

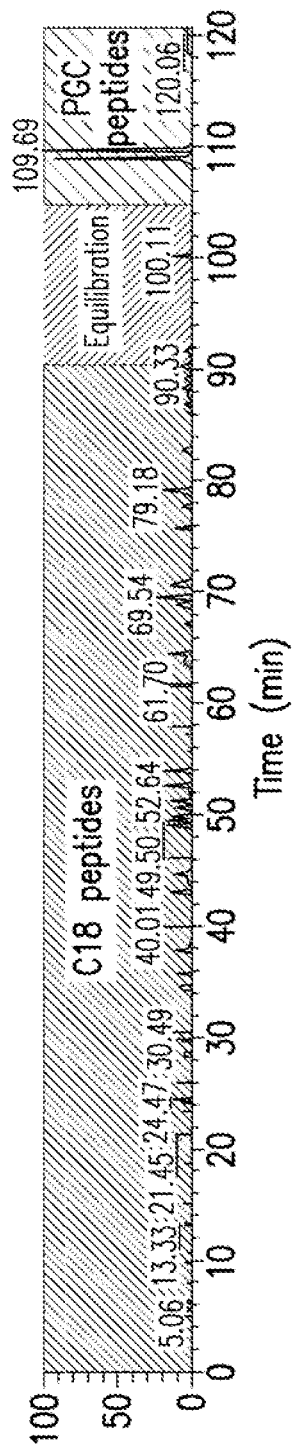
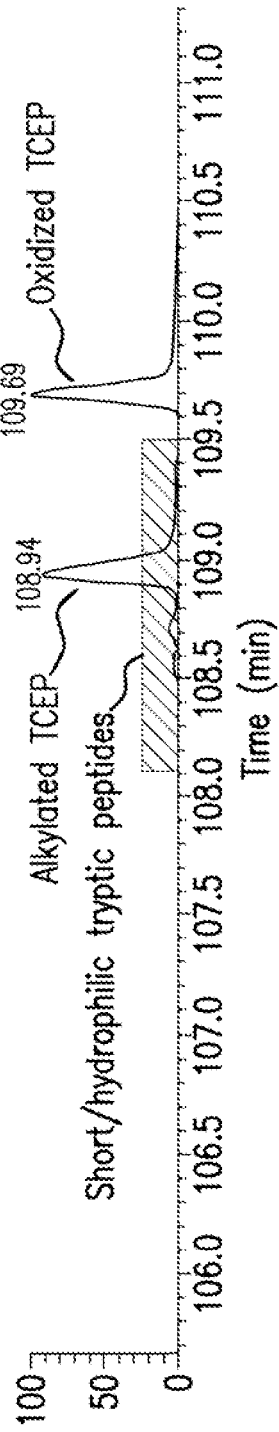

DUAL-COLUMN LC-MS SYSTEM AND METHODS OF USE THEREOF

CROSS REFERENCE TO RELATED APPLICATIONS

This application is a continuation of U.S. patent application Ser. No. 17/125,342, filed on Dec. 17, 2020, which is a continuation of U.S. patent application Ser. No. 16/260,471, filed on Jan. 29, 2019, which claims benefit of and priority to U.S. Provisional Patent Application No. 62/624,352 filed on Jan. 31, 2018, all of which are incorporated herein by reference in their entirety.

FIELD OF THE INVENTION

The invention is generally related to systems and methods for improved protein sequencing.

BACKGROUND OF THE INVENTION

Confirmation of the primary sequence of therapeutic monoclonal antibodies (mAbs) by liquid chromatography-mass spectrometry (LC-MS) analysis after tryptic digestion is an essential assay routinely performed in the biotechnology industry. Complete sequence coverage is highly desirable for peptide mapping analysis of therapeutic monoclonal antibodies, but it is not always achievable by tryptic digestion alone. Small and/or hydrophobic peptides with poor or no retention on the commonly used C18 column often miss MS detection, resulting in gaps in the coverage map. It is particularly problematic if the missed sequence belongs to critical complementarity-determining regions. To achieve 100% coverage, a secondary enzymatic digestion is frequently required. Alternatively, the emerging capillary zone electrophoresis coupled to mass spec (CE-MS) technology can achieve 100% coverage, but availability of such platforms is still limited.

Therefore, it is an object of the invention to provide systems and methods for obtaining complete amino acid sequences of proteins.

SUMMARY OF THE INVENTION

A dual-column liquid chromatograph-mass spectrometry (LC-MS) system and methods of use thereof are provided. One embodiment provides a dual column liquid chromatography system including a first column in fluid communication with a first multi-port switching diverter valve; a second column in fluid communication with the first multi-port switching diverter valve; a second multi-port switching diverter value in fluid communication with the first multi-port switching diverter valve; a mass spectrometer in fluid communication with the second multi-port switching diverter valve; a collection vessel in fluid communication with the second multi-port switching diverter valve; and a computer in electronic communication with the dual column chromatography system for controlling fluid flow through the system by configuring the ports of the first and second multi-port switching diverter valves in multiple configurations. The system can optionally include a detector, for example a UV detector and/or a mass spectrometer, and a collection vessel. Typically, the first column is packed with material for separating non-polar and hydrophobic peptides and the second column is packed with material for separating polar peptides. For example, the first column can be a C18 column and the second column can be a porous graphitic column.

In another embodiment the multi-port switching diverter valves are configured to allow fluid from the first column to flow through the second column. In still another embodiment, the multi-port switching diverter valves are configured to allow fluid from the first column to bypass the second column and flow to a mass spectrometer.

Another embodiment provides a method for determining the sequence of a protein by digesting the protein to produce peptide fragments of the protein, loading the peptide fragments onto a first high performance liquid chromatography column under conditions in which some of the peptide fragments are retained on the first column and some of the peptide fragments are not retained on the first column. The peptides not retained on the first column flow directly into a second high performance liquid chromatography column where at least a portion of the peptides not retained on the first column are retained on the second column. The method includes eluting the peptides retained on the first column in a way in which the eluted peptides bypass the second column. The eluted peptides are analyzed by mass spectrometry to determine the amino acid sequence of the peptides. Peptides from the second column are also eluted and analyzed by mass spectrometry to determine the amino acid sequence of the eluted peptides. The combined sequences of the eluted peptides from the first and second columns provide a complete amino acid sequence of the protein. In one embodiment, the protein being sequenced is an antibody, for example a monoclonal antibody, or a fusion protein.

In another embodiment the first column is packed with material for separating non-polar peptides and the second column is packed with material for separating polar peptides. For example, the first column can be a C18 column and the second column can be a porous graphitic column. In certain embodiments, the protein is reduced and alkylated prior to digestion. The proteins are typically enzymatically digested, for example using trypsin.

In one embodiment, peptides eluted from the C18 column are analyzed by mass spectrometry at a scan range of 300 to 2000 m/z and peptides eluted from the PGC column is analyzed by mass spectrometry at a scan range of 200 to 2000 m/z.

BRIEF DESCRIPTION OF THE DRAWINGS

FIG. 4 is a table showing a representative example of a C18-PGC elution gradient.

FIG. 6A is a screen shot of a user interface showing parameters for C18 elution.

FIGS. 7A-7B are an exemplary total ion chromatogram (TIC) of the C18-PGC peptide mapping analysis.

DETAILED DESCRIPTION OF THE INVENTION

I. Definitions

Figure 1:
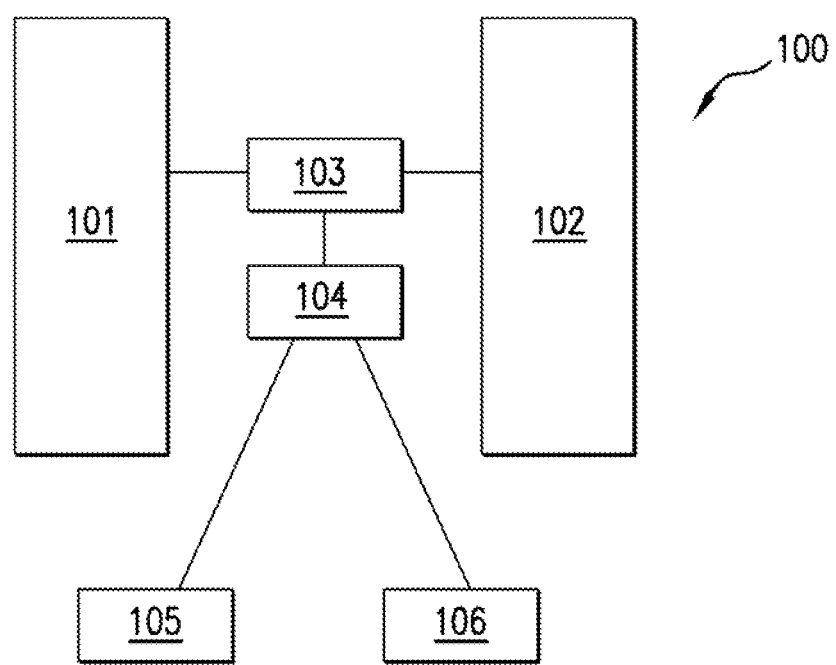
FIG. 1 is a diagram of an exemplary dual column LC-MS system.

As used herein, "peptide mapping" refers to the technique of characterizing proteins and elucidating their primary amino acid structures. It is a widely utilized technique to characterize monoclonal antibodies and other recombinant protein pharmaceuticals.

As used herein, "tryptic peptides" refer to peptides that are generated by digesting larger proteins into smaller peptides using the serine protease trypsin. Trypsin cleaves proteins into peptides with an average size of 700 to 1500 Daltons by hydrolyzing peptide bonds on the carboxy terminal side of arginine and lysine amino acid residues.

As used herein, "porous graphitic carbon (PGC) column" refers to a chromatography column that is composed of porous graphite carbon. It is a good stationary phase in liquid chromatography for its unique retention and separation of very polar compounds.

As used herein, "C18 column" refers to a reverse phase chromatography column commonly used in liquid chromatography. C18 columns consist of carbon chains bonded to silica particles within the column. These columns are commonly used to separate hydrophobic and non-polar molecules, which bind to the carbon chains of the silica.

As used herein, "liquid chromatography (LC)" refers to a technique used to separate, identify, and quantitate components in a mixture. In column liquid chromatography, the liquid mobile phase passes through the column and components of the mobile phase interact with the solid stationary phase. The composition of the mobile phase can be changed during a separation run to alter the strengths of interactions of the compounds of interest. As the mobile phase continues to flow through the column, the eluent is typically collected in fractions while monitoring the concentrations of the compounds eluted from the column over time to produce an elution curve, or chromatogram.

Liquid chromatography is commonly coupled with mass spectrometry to continuously measure the protein elution from the column by measuring light absorption at 280 nm by the amino acid tryptophan. Each distinct peak on a chromatogram represents a unique component resolved by the column, and the area under the peak corresponds to the amount of that compound eluted from the column. A single peak could contain multiple proteins so often further analysis of the eluted fractions is necessary.

As used herein, "stationary phase" refers to the substance that stays fixed in the column. The most commonly used stationary phase columns are carbon chain-bonded silica, phenyl-bonded silica, and cyano-bonded silica.

As used herein, "mobile phase" and "liquid phase" can be used interchangeably and refer to mixtures of water or aqueous buffers and organic solvents that are used to elute compounds from columns. The most common mobile phase solvents include but are not limited to acetonitrile, methanol, tertrahydrofuran, ethanol, or isopropyl alcohol.

As used herein, "elution", "eluting", and "eluted" refer to the process of extracting one material from another by washing with a solvent.

As used herein, "total ion chromatogram (TIC)" is a type of chromatogram created by summing up the intensities of all the mass spectral peaks belonging to the same scan. The TIC includes background noise as well as sample components.

As used herein, "TFA" is an abbreviation for trifluoroacetic acid, a commonly used modifier for peptide separation in reverse-phase liquid chromatography. Modifiers are substances added to the mobile phase that interact with both the stationary phase and sample to alter retention.

The term "LC-MS" refers to an analytical chemistry technique that combines the physical separation capabilities of liquid chromatography (or HPLC) with the mass analysis capabilities of mass spectrometry (MS).

II. Dual-Column LC-MS System

In a standard peptide mapping configuration, peptides are retained on a C18 column installed on a LC system, and eluted to the mass spectrometer using one 6-port switching divert valve, which switches between direct LC flow to the mass spectrometer or to the waste container.

One embodiment provides a dual column liquid chromatography system including a first column in fluid communication with a first multi-port switching diverter valve; a second column in fluid communication with the first multi-port switching diverter valve; a second multi-port switching diverter value in fluid communication with the first multi-port switching diverter valve; a mass spectrometer in fluid communication with the second multi-port switching diverter valve; a collection vessel in fluid communication with the second multi-port switching diverter valve; and a computer in electronic communication with the dual column chromatography system for controlling fluid flow through the system by configuring the ports of the first and second multi-port switching diverter valves in multiple configurations.

The system can optionally include a detector, for example a UV detector and or a mass spectrometer, and a collection vessel. Typically the first column is packed with material for separating non-polar peptides and the second column is packed with material for separating polar peptides. For example, the first column can be a C18 column and the second column can be a porous graphitic column.

In another embodiment the multi-port switching diverter valves are configured to allow fluid from the first column to flow through the second column. In still another embodiment, the multi-port switching diverter valves are configured to allow fluid from the first column to bypass the second column and flow to the mass spectrometer.

FIG. 1 is a diagram of an exemplary system 100. System 100 contains column 101. Column 101 is typically an HPLC column packed with material for separating non-polar and/or hydrophobic peptides. Column 101 is in fluid communication with multi-port switching diverter valve 103. System 100 also includes a second column 102 also in fluid communication with multi-port switching diverter valve 103. Multi-port 103 is in fluid communication with second multi-port switching diverter valve 104. Multi-port switching diverter valve 104 is in fluid communication with mass spectrometer 106 and collection vessel 105.

A. Dual Diverter Valves

Figure 2:
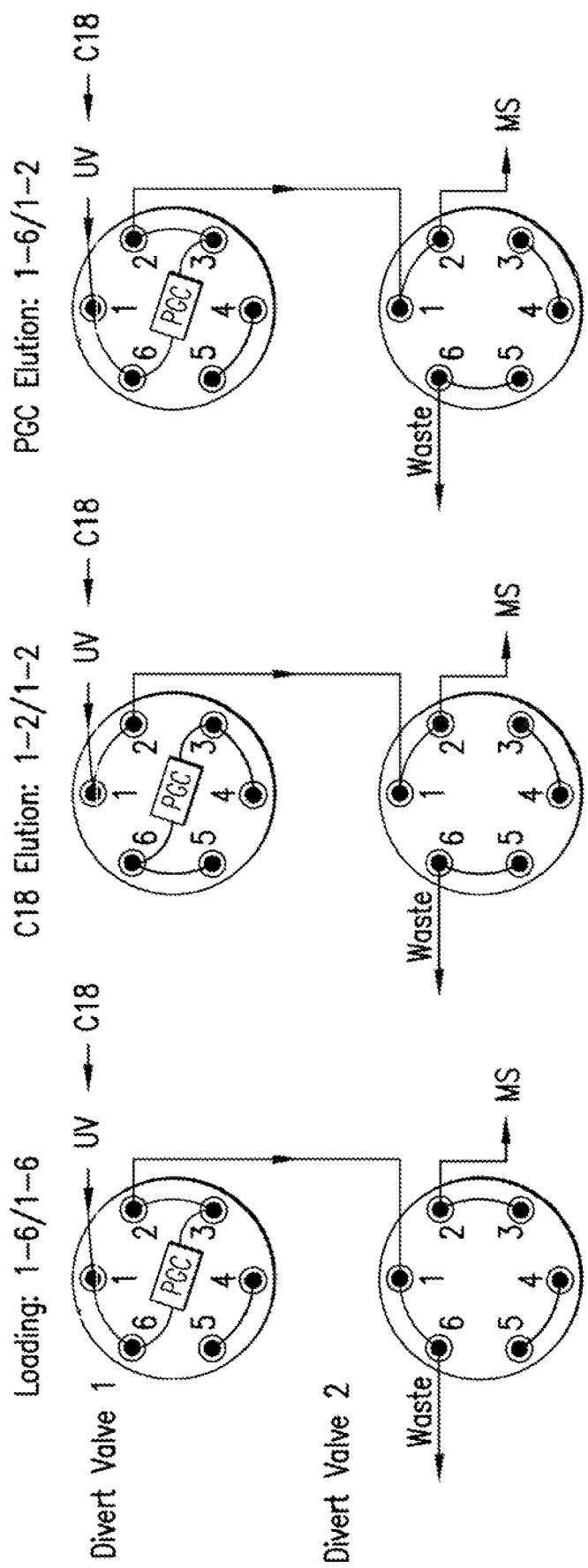
FIGS. 2A-2C are schematic diagrams of the dual diverter valve configuration. The lines indicate solvent flow path when divert valves are configured in either "Loading", "C18 elution", or "PGC elution" modes. The "1-x/1-x" position refers to port positions of divert valves 1 and 2, respectively.
Figure 5A:
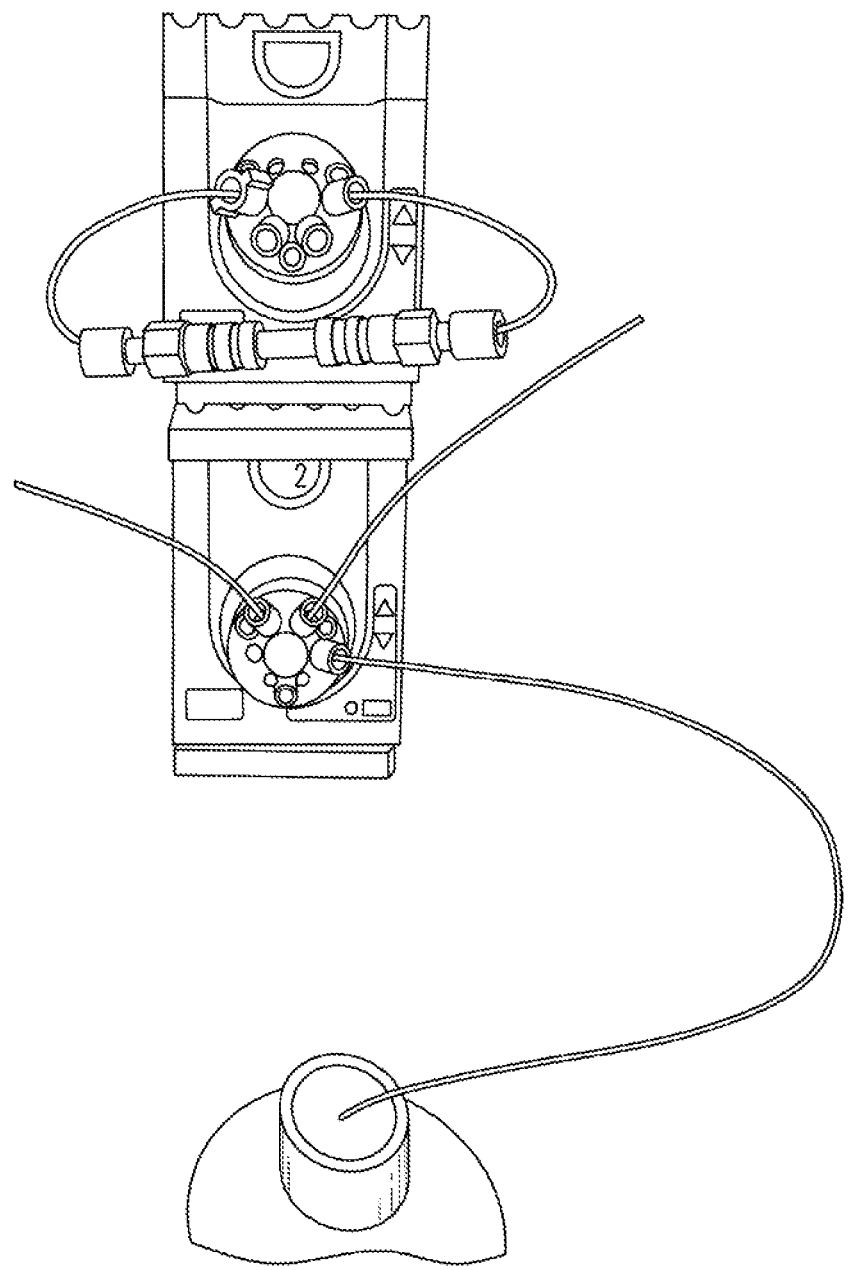
FIGS. 5A and 5B are photographs of a first multi-port switching diverter valve on top of a second multi-port switching converter valve.
Figure 5B:
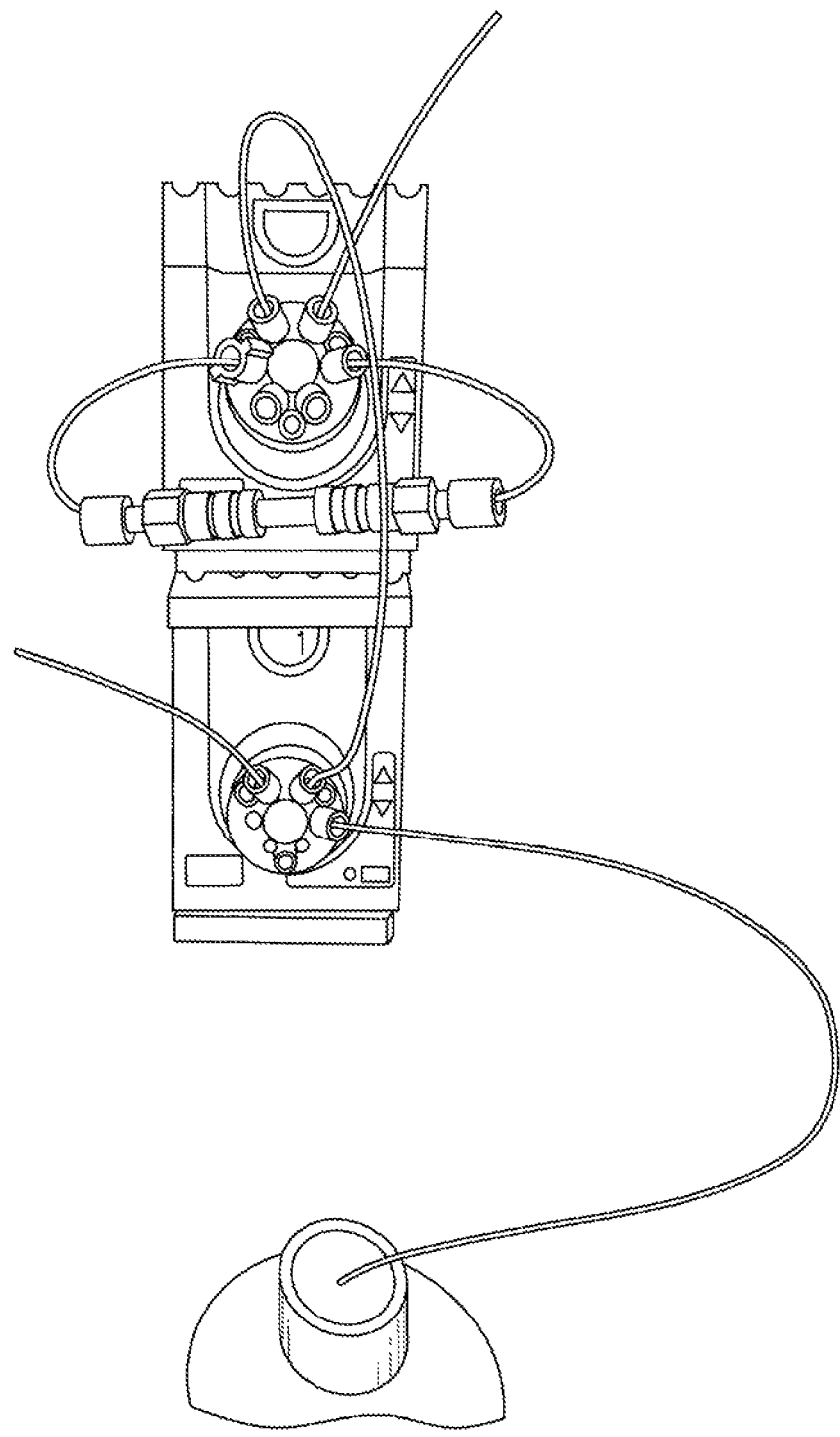

A representative configuration of the two switching divert valves is shown in FIGS. 2A-2C. FIGS. 5A and 5B are photographs of exemplary dual diverter valves. The first position of the diverter valve is referred to as "1-6", in which solvent flow enters through port 1 and exits through port 6. The second position of the diverter valve is "1-2", in which solvent flow enters through port 1 and exits through port 2.

The "1-x/1-x" position refers to port positions of divert valves 1 and 2, respectively. Therefore, for example "1-6/1-6" indicates that solvent from LC is entering port 1 and exiting from port 6 of diverter valve 1, then enters port 1 and exits from port 6 of diverter valve 2. The first diverter valve is plumbed such that the "1-6" position will direct flow from the LC through the PGC column and into the inlet of the second diverter valve. Connections to the PGC column are located at ports 6 and 3 of the diverter valve 1 as shown in FIG. 2A. More specifically, the outlet line from the LC is connected to port 1 of diverter valve 1, the PGC column is connected at ports 3 and 6 with flow direction from port 6 to port 3, and an outlet line from port 2 of diverter valve 1 that is connected to port 1 of diverter valve 2. The second diverter valve is plumbed such that the "1-6" position directs flow from the outlet of diverter valve 1 and into the mass spectrometer, while the "1-2" position redirects flow to waste. More specifically, the outlet line of diverter valve 1 is connected at port 1, the outlet line of diverter valve 2 connects port 2 to the mass spectrometer, and an outlet line connects port 6 to the waste. Peptides can be loaded to both the C18 column and the PGC column in the "1-6/1-6" position.

Elution of tryptic peptides from the C18 column would occur in the "1-2/1-2" position, as described in FIG. 2B. Peptide elution from the PGC column would occur in the "1-6/1-2" position, as described in FIG. 2C.

In one embodiment, the flow rate through the dual-column LC-MS system can be 0.25 mL/min. It will be appreciated one skilled in the art that other flow rates used in typical LC-MS can be used in the disclosed systems.

In one embodiment, the mobile phase is 0.05% TFA in water for loading, and 0.045% TFA in acetonitrile for the elution phase. A representative elution gradient is show in FIG. 4.

In one embodiment 0.1% formic acid (FA) was used for loading and 0.1% formic acid in acetonitrile was used for elution.

Figure 3:
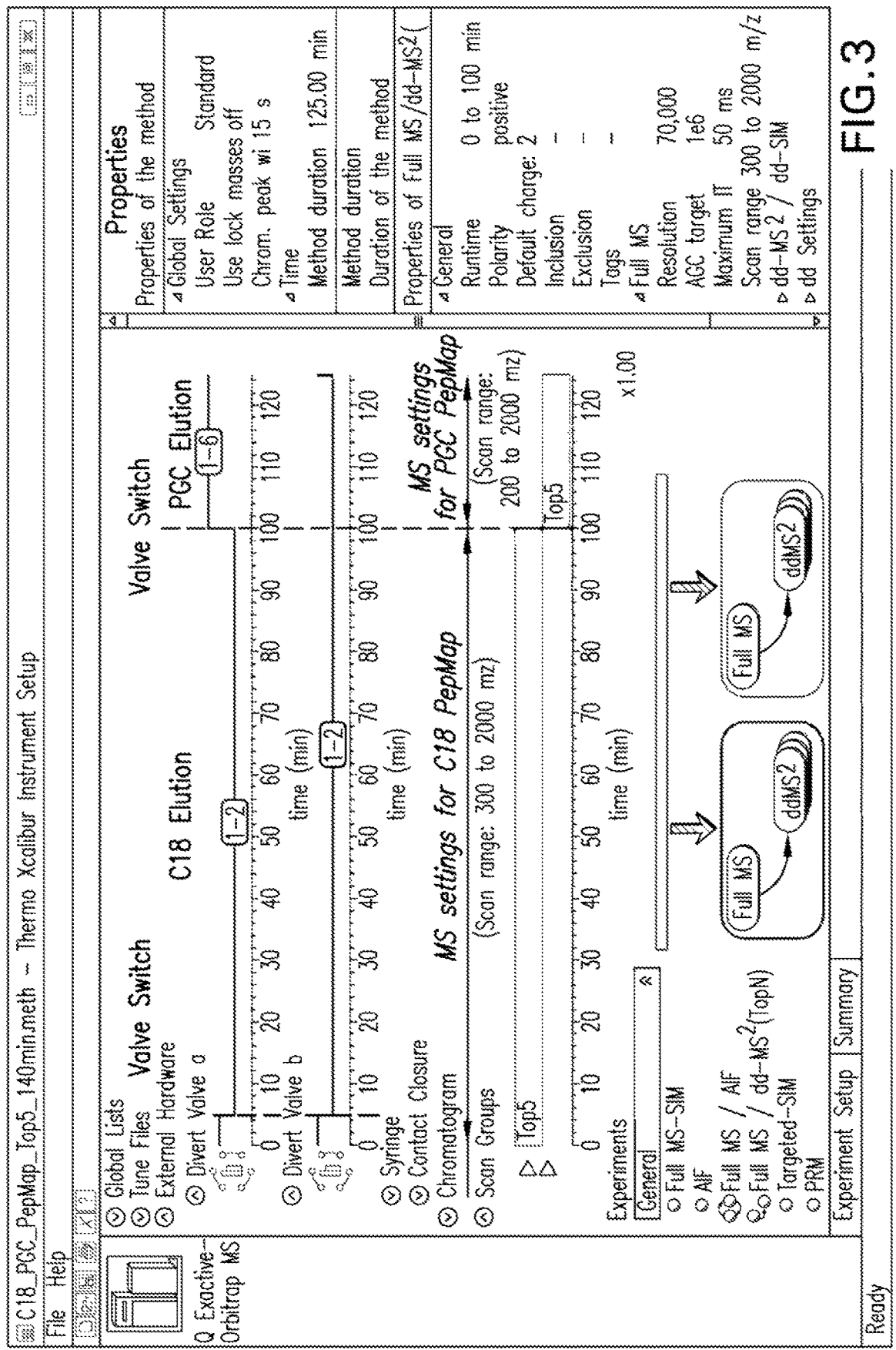
FIG. 3 is an image of a user interface showing an exemplary mass spectrometer method setup for data acquisition for dual column PGC-C18 configuration.

The switching of the diverter valve positions can be controlled in the mass spectrometer setup as shown in FIG. 3. Timing of the switches is correlated with the C18-PGC LC gradient, an example of which is shown in FIG. 3.

B. Peptide Elution

Figure 6A:
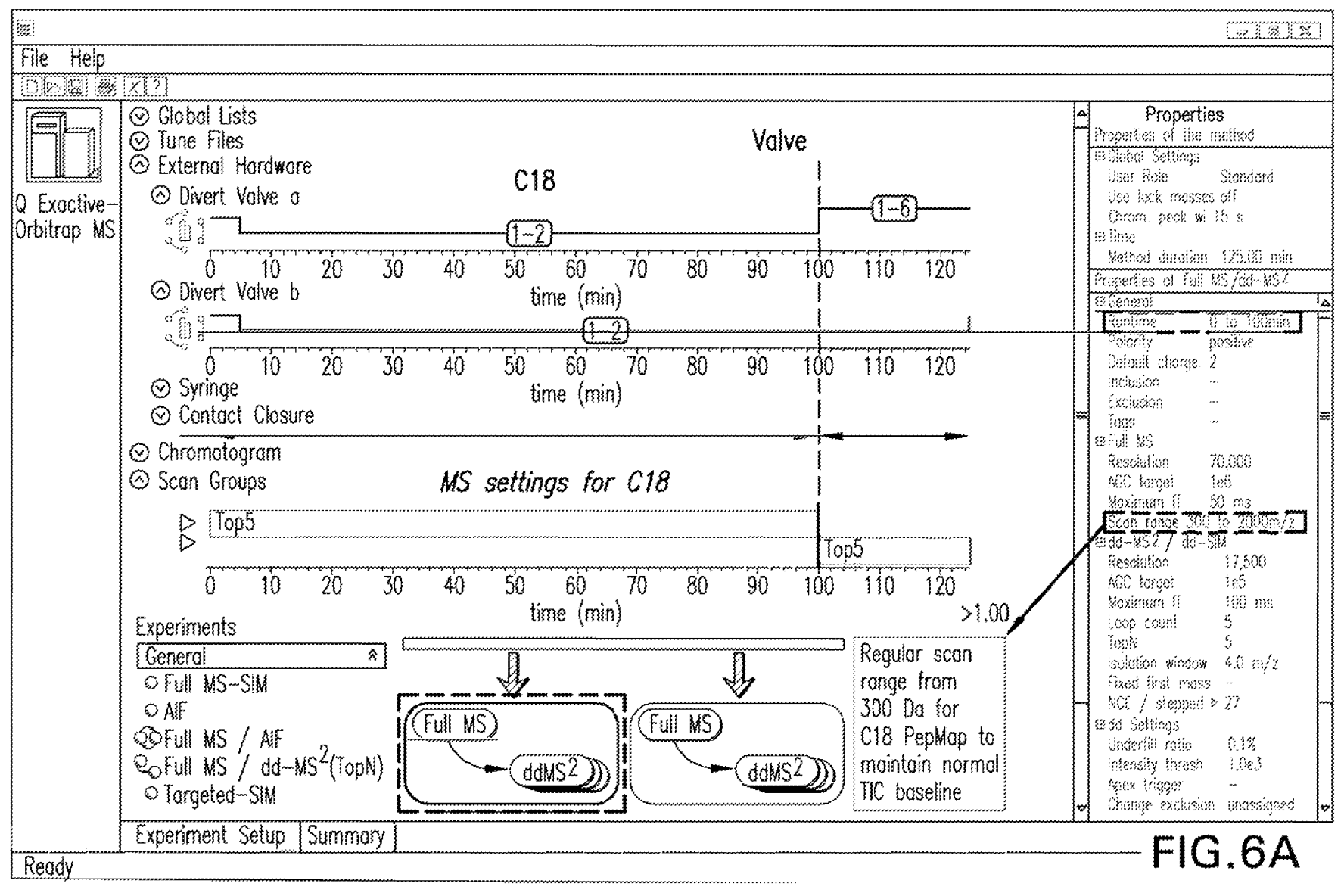
Figure 6B:
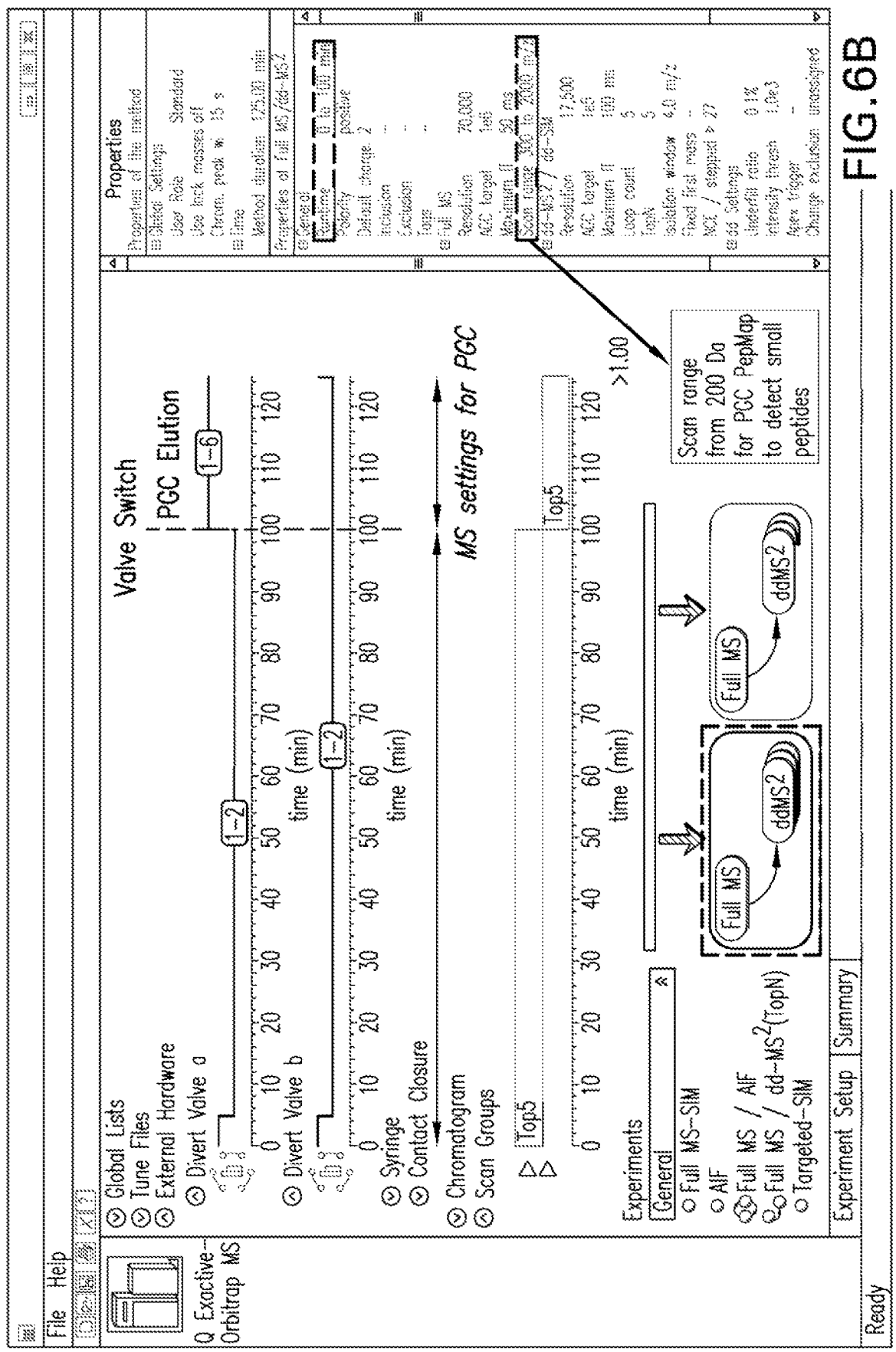
FIG. 6B is a screen shot of a user interface showing parameters for PGC elution.

In one embodiment, proteins are sequenced using the dual-column LC-MS system disclosed herein. The proteins are typically reduced and alkylated using TCEP and iodoacetamide and then digested with trypsin to produce tryptic peptides. The loading and elution of tryptic peptides from the C18 column and PGC column can be achieved sequentially. For example, tryptic digests are injected to the LC-MS and then loaded to both the C18 and PGC columns with diverter valves in the "1-6/1-6" position. Tryptic peptides are first retained on the C18 column. Hydrophilic peptides that are not retained on the C18 column are then eluted on the downstream PGC column and are retained on the PGC column. FIGS. 6A and 6B show exemplary elution parameters. After the loading step, peptide elution first occurs on the C18 column, with the diverter valves set to bypass the PGC column using the "1-2/1-2" position. After the elution on the C18 column is complete, the gradient is equilibrated to the initial condition. The elution of PGC column occurs by diverting the flow through the PGC column by using the divert valves in the "1-6/1-2" position. C18 elution must occur while bypassing the downstream PGC column to avoid clogging of the PGC column with larger tryptic peptides retained on the C18 column or obscuring signal of the small, hydrophilic peptides retained on the PGC column.

C. Mass Spec Analysis

The peptide eluent from both the C18 and PGC columns flow to the mass spectrometer for MS analysis. In one embodiment, the scan range for C18 eluent is set from 300 to 2000 m/z to maintain normal TIC baseline. In one embodiment, the scan range for PGC eluent is set to 200 to 2000 m/z to detect small peptides. The disclosed methods have been shown to provide 100% sequence coverage for all of the molecules tested.

The dual column LC-MS system can be implemented with minor modifications to current C18 peptide mapping set ups, while yielding more sequence coverage and valuable information. Hence, the dual-column LC-MS system offers a simple solution to achieve complete sequence coverage of mAbs in a single LC-MS analysis.

EXAMPLES

Example 1: Analysis of Sequence Coverage

Methods:

Monoclonal antibody samples were first reduced and alkylated using TCEP and iodoacetamide before digestion with trypsin. The digestion mixtures were then injected onto the dual-column LC-MS system consisting of a C18 column and a PGC column. During the loading step, tryptic peptides were first retained onto a C18 column. Hydrophilic peptides not retained on this column were eluted and retained onto a downstream PGC column. The elution first occurred on the C18 column while a diverting valve allowed the flow to bypass the PGC column. After the elution on C18 column was complete and the gradient was equilibrated to the initial condition, the elution of peptides on the PGC column was started by diverting the flow through the PGC column.

Results:

It was observed that common peptides retained on the PGC column, but not on the C18 column, were dipeptides containing a C-terminal Lys or Arg. By using accurate MS1 masses and signature immonium ions during HCD fragmentation, the identities of those short peptides can be confidently confirmed. Using the NIST mAb reference standard and multiple in-house mAb molecules, it was demonstrated that the disclosed method can provide 100% sequence coverage for all molecules tested. FIG. 7 shows a total ion chromatogram of an exemplary protein that was sequenced.

We claim:

1. A method for determining the sequence of a protein comprising:

loading the peptide fragments onto a first high performance liquid chromatography column comprising material for separating non-polar peptides under conditions in which a portion of the peptide fragments are retained on the first column and a portion of the peptide fragments are not retained on the first column, wherein the peptides not retained on the first column flow directly into a second high performance liquid chromatography column comprising material for separating polar peptides, wherein at least the portion of the peptide fragments not retained on the first column are retained on the second column;

eluting the portion of the peptide fragments retained on the first column;

eluting the portion of the peptide fragments retained on the second column; and analyzing the portion of the peptide fragments retained on the first column and the portion of the peptide fragments retained on the second column to determine the amino acid sequence of the portion of the peptide fragments retained on the first column and the portion of the peptide fragments retained on the second column.

2. The method of claim 1, wherein the portion of the peptide fragments retained on the first column bypass the second column.

3. The method of claim 1, wherein the portion of the peptide fragments retained on the first column and the portion of the peptide fragments retained on the second column are analyzed by mass spectrometry.

4. The method of claim 1, wherein the portion of the peptide fragments retained on the first column and the portion of the peptide fragments retained on the second column are analyzed by a UV detector.

5. The method of claim 1, wherein the amino acid sequence of the portion of the peptide fragments retained on the first column and the portion of the peptide fragments retained on the second column, when combined, provide a complete amino acid sequence of the protein.

6. The method of claim 1, wherein the peptide fragments are loaded onto the first column using 0.1% formic acid (FA).

7. The method of claim 1, wherein the portion of the peptide fragments retained on the first column and the portion of the peptide fragments retained on the second column are eluted using 0.1% formic acid in acetonitrile.

8. The method of claim 1, wherein the peptide fragments are loaded onto the first column using 0.05% trifluoroacetic acid (TFA).

9. The method of claim 1, wherein the portion of the peptide fragments retained on the first column and the portion of the peptide fragments retained on the second column are eluted using 0.045% TFA.

10. The method of claim 1, reducing and alkylating the protein with tris(2-carboxyethyl)phosphine (TCEP) and iodoacetamide prior to digesting the protein to produce peptide fragments.

11. The method of claim 1, wherein the first column is a C18 column.

12. The method of claim 1, wherein the second column is a porous graphitic column (PGC).

13. The method of claim 11, wherein the portion of the peptide fragments eluted from the C18 column is analyzed by mass spectrometry at a scan range of 300 to 2000 m/z.

14. The method of claim 12, wherein the peptides eluted from the PGC column is analyzed by mass spectrometry at a scan range of 200 to 2000 m/z.

15. A dual column liquid chromatography system for determining the sequence of a protein comprising:
a first column in fluid communication with a first multi-port switching diverter valve, wherein the first column comprises material for separating non-polar peptides;
a second column in fluid communication with the first multi-port switching diverter valve, wherein the second column comprises material for separating polar peptides;
a second multi-port switching diverter value in fluid communication with the first multi-port switching diverter valve; and
a computer in electronic communication with the dual column chromatography system for controlling fluid flow through the system by configuring the ports of the first multi-port switching diverter valve and the second multi-port switching diverter valve in multiple configurations.

16. The system of claim 15, wherein the protein is reduced and alkylated with tris(2-carboxyethyl)phosphine (TCEP) and iodoacetamide prior to digestion.

17. The system of claim 15, further comprising:
a mass spectrometer in fluid communication with the second multi-port switching diverter valve; and
a collection vessel in fluid communication with the second multi-port switching diverter valve.

18. The system of claim 15, wherein the first multi-port switching diverter valve and the second multi-port switching diverter valve each comprise 1-6 ports.

19. The system of claim 15, wherein the first column is a C18 column.

20. The system of claim 15, wherein the second column is a porous graphitic column (PGC).

* * * * *